United States Patent [19]

Mancini et al.

[11] 4,180,308
[45] Dec. 25, 1979

[54] CONTACT LENS

[75] Inventors: William L. Mancini, Framingham; Donald R. Korb, Boston; Miguel F. Refojo, Lexington, all of Mass.

[73] Assignee: Syntex (USA) Inc., Palo Alto, Calif.

[21] Appl. No.: 736,555

[22] Filed: Oct. 28, 1976

Related U.S. Application Data

[63] Continuation-in-part of Ser. No. 685,996, May 13, 1976, Pat. No. 4,056,496, which is a continuation-in-part of Ser. No. 451,906, Mar. 18, 1974, Pat. No. 3,957,362, which is a continuation-in-part of Ser. No. 294,019, Oct. 2, 1972, abandoned.

[51] Int. Cl.$^2$ .......................... G02C 7/04; C08L 00/00
[52] U.S. Cl. .......................... 351/160 H; 260/29.6 TA; 526/273
[58] Field of Search .............. 351/160, 160 H, 160 R; 260/29.6 TA; 526/273

[56] References Cited

U.S. PATENT DOCUMENTS 3,985,697  10/1976  Urbach ............................ 351/160 X

FOREIGN PATENT DOCUMENTS 986343   3/1976  Canada ................................. 351/160
2426701 12/1975  Fed. Rep. of Germany .......... 351/160

OTHER PUBLICATIONS

Knoll, H. A., Progress Report on Softlens Contact Lenses, reprinted from a speech given at Ohio State University, 9/27/68.

Primary Examiner—Conrad J. Clark
Attorney, Agent, or Firm—Robert L. Goldberg; George W. Neuner

[57] ABSTRACT

This invention concerns a minus prescription hydrogel contact lens that permits oxygen diffusion to the cornea in sufficient quantity to avoid the effects of oxygen deprivation; avoids the physiological complications arising from damage to the bulbar conjunctiva due to compression of the limbal capillaries; and avoids corneal scleral or wetting deficiencies. These advantages are accomplished through a combination of lens design and hydrogel properties.

25 Claims, 1 Drawing Figure

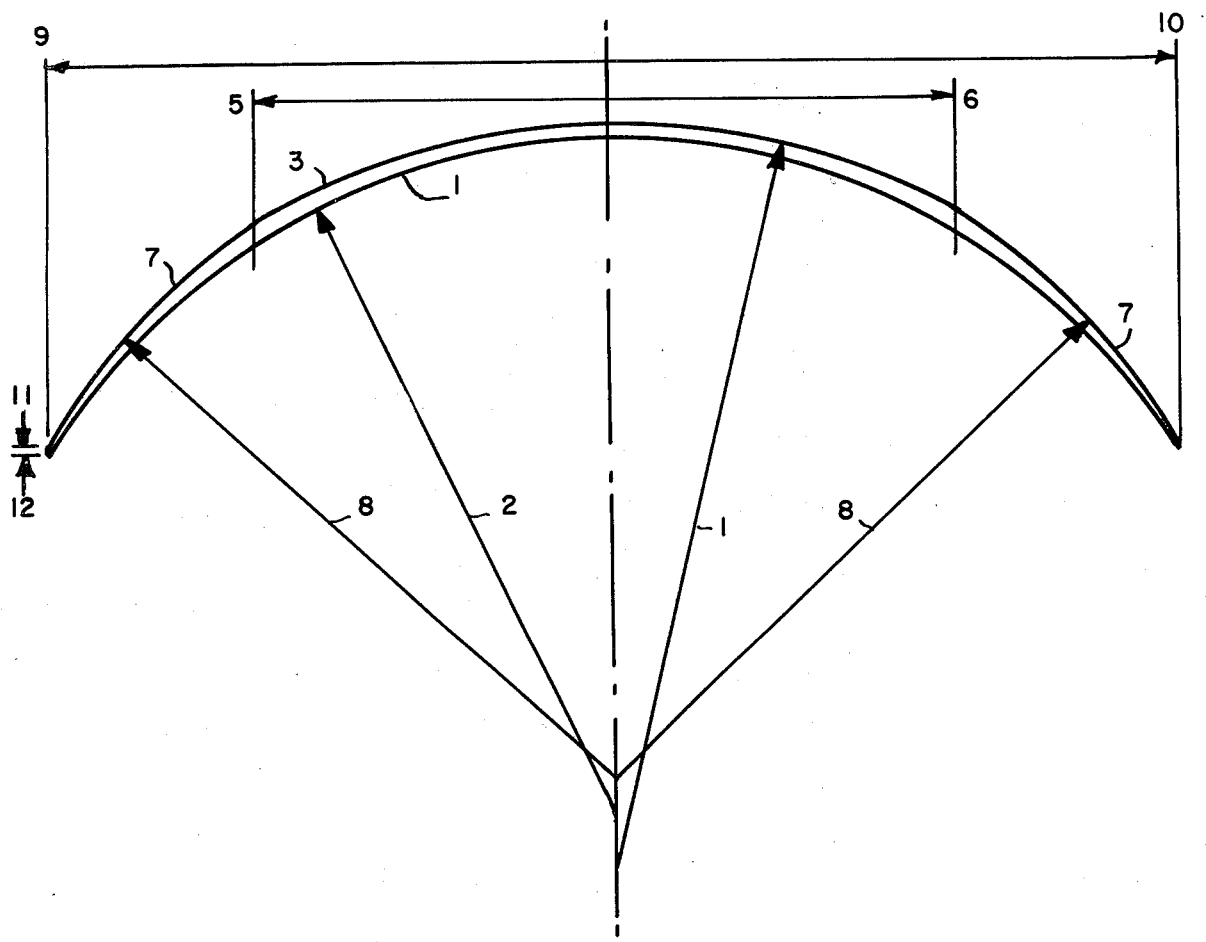

1

CONTACT LENS

CROSS-REFERENCE TO RELATED APPLICATIONS

This application is a continuation-in-part of copending United States patent application Ser. No. 685,996, now U.S. Pat. No. 4,056,496 filed May 13, 1976 which application is a continuation-in-part of application Ser. No. 451,906, now U.S. Pat. No. 3,957,362. Application Ser. No. 451,906 filed Mar. 18, 1974 was a continuation-in-part of U.S. Pat. Application Ser. No. 294,019, filed Oct. 2, 1972 and now abandoned.

BACKGROUND OF THE INVENTION

1. Field of the Invention

This invention relates to soft hydrogel contact lenses and more specifically, is directed to soft contact lens design.

2. Description of the Prior Art

As is known in the art, contact lenses are frequently made from polymethyl methacrylate. Such lenses are known as the "hard lenses". Many people cannot adapt to the presence of a hard lens in the eye and with others, the lens compromises the physiological processes required for corneal metabolism. More recently, new soft lens materials have been developed which avoid some of the problems associated with the hard lens. One class of such lens materials is described in U.S. Pat. Nos. 2,976,567 and 3,220,960 incorporated herein by reference. These materials are hydrogels of a sparingly cross-linked hydrophilic copolymer comprising a major amount of a monoester of an olefinic acid from the group of acrylic and methacrylic acids having a single olefinic double bond and a minor amount of a polymerizable diester of one of said acids, the diester having at least two olefinic double bonds. A preferred hydrogel disclosed in the aforesaid patent is a slightly cross-linked material comprising a predominant quantity of 2-hydroxyethyl methacrylate. The hydrogel, known as "hema", is used for contact lens fabrication because of its ability to absorb water of hydration, typically from about 35 to 65% by weight of the hydrogel. The water renders the lens flexible and soft which properties enable it to mold to the curvature of the eye. This is in contrast to the conventional hard lens which maintains a rigid configuration that does not always conform to the eye's curvature.

In U.S. Patent Application Ser. No. 685,996, filed May 13, 1976 now U.S. Pat. No. 4,056,496, assigned to the same assignee as the subject application and incorporated herein by reference, hydrogels are disclosed which are also suitable for soft lens fabrication. The hydrogels are formed from a hydrophilic monomer from the group of dihydroxyalkyl acrylates and methacrylates (collectively the "dihydroxy acrylate"), a substantially water insoluble monomer from the group of alkyl acrylates and methacrylates (collectively "the acrylate") and preferably, a minor amount of an epoxidized alkyl acrylate or methacrylate (collectively the "epoxidized acrylate"). The dihydroxyalkyl acrylate is preferably used in major amount, the alkyl acrylate in minor amount, and the epoxidized acrylate in an amount sufficient to impart the desired rigidity. The polymer is formed by a free radical, bulk polymerization process in the substantial absence of solvent in order to obtain a polymer suitable for fabrication of a contact lens.

Numerous other soft lens materials are known and include cross-linked poly(hydroxyethyl methacrylate) and a cross-linked copolymer of hydroxyethyl methacrylate grafted onto a poly (vinyl pyrrolidone) backbone. Still other soft lens materials and processes for their formation are reported in the following U.S. Pat. Nos. 3,532,679; 3,639,524; 3,647,736; 3,721,657; 3,758,448; 3,767,731; 3,772,235; 3,803,093; 3,816,571; 3,822,196; 3,839,304 and 3,841,985, all incorporated herein by reference.

It is known in the art that the conventional hard contact lenses and many of the contemporary soft hydrogel lenses may only be worn for a short duration of time, typically for periods of time up to twelve hours. It is further known that extended wear, for periods in excess of twelve hours, particularly during closed-eye periods (during sleeping hours) may cause long term injury to the eye.

One cause of injury resulting from extended wear of the above lenses is the lens resting on the bulbar conjunctivia for an extended time. Due to the weight of the lens, the peripheral areas of the lens compress the vascular system thereby compressing the limbal capillaries causing physiological complications. One approach at solving this problem has been the use of wider band and flatter posterior curvatures which result in looser fitting lens. However, this approach has not been notably successful because the loose fit results in lens movement when blinking occurs.

Another cause of injury arising from extended wear of such lenses is corneal-scleral wetting deficiences resulting in dry areas of the corneal-scleral tissue. This problem may be caused by alterations in the normal blinking mechanism that either reduces the frequency of blinks or alters the ability of the lids to make a complete closure upon blinking. Additionally, many lens designs create breaks in the normal lid cornea contact necessary for the required evenly distributed wiping and spreading of the tears over all of the corneal-scleral tissue. This problem is usually encountered in the areas of the tissue immediately peripheral to the edge of the lens.

Perhaps the most serious cause of injury arising from extended wear of the aforesaid lenses is oxygen deprivation due to the lens covering a significant portion of the corneal surface thus acting as a barrier to contact of the cornea with an oxygenated tear layer. This results in oxygen deprivation at the cornea and interferes with the metabolic and physiological requirements of the cornea.

It is known that the cornea requires a supply of oxygen at its surface and relies upon oxygen diffusion from a tear layer over its surface for almost all of its required supply. During open-eye periods, the tear layer is oxygenated by atmospheric oxygen. During closed-eye periods, the tear layer is oxygenated by the capillaries of the eyelid rather than oxygen from the atmosphere as when the eye is open. The partial pressure of oxygen supplied from the capillaries is less than about $\frac{1}{3}$ that supplied by the atmosphere. In the absence of a lens acting as a barrier, the oxygen supply to the cornea, both during open-eye and closed-eye periods, is sufficient. In this respect, Mandell and Polse, in "Critical Oxygen Tension at the Corneal Surface", Archives of Opthamology, 84, 505 (1970), have determined that the minimum partial pressure of oxygen needed at the surface of the cornea to maintain normal corneal physiology is 15 mm Hg or a supply rate of about 3.5 $\mu l/cm^2$- hr. Others have stated that this minimum rate is 6.0 $\mu l/cm^2$-hr.

From the aforesaid, it is clear that a contact lens capable of continuous wear should provide at least 3.5 $\mu l/cm^2$-hr, preferably 6 $\mu l/cm^2$-hr of oxygen to the corneal surface to avoid the physiological complication arising from oxygen deprivation. Hard contact lenses, such as those of methyl methacrylate, are not permeable to oxygen, but through known lens design, permit some circulation of air to the corneal surface. Such design features may comprise a tear pump mechanism whereby oxygenated tears are pumped beneath the lens with each blink of the eyelid and/or central or paracentral apertures whereby there is actual atmospheric contact with the cornea. Contemporary hydrogel lenses, though permeable to oxygen through the interstitial spaces of the hydrogel material, are not sufficiently permeable to fully oxygenate the cornea in the cross-sections in which they are fabricated. Hence, oxygen deprivation is also encountered with these lenses.

The circulation of some oxygen using the aforesaid lenses permits daily wear of the same with minimal non-reversible damage to corneal physiology. However, during closed-eye periods, when the oxygen supply is reduced to less than ⅓ the level of opened-eye condition, known lens design does not permit sufficient transfer of oxygen to the corneal surface to permit wear without oxygen deprivation.

The above problems have caused the art to seek alternative means for supplying required oxygen to the corneal surface. One such attempt is described in U.S. Pat. No. 3,551,035, incorporated herein by reference. In this patent, a rigid (hard) lens material is used which material, unlike the methyl methacrylate hard lens, is permeable to oxygen. However, this lens suffers other disadvantages of hard lenses and consequently, in U.S. Pat. No. 3,619,044, also incorporated herein by reference, the patentee attempts to overcome the disadvantages of the hard lens by grafting soft lens material onto the peripheral edge of the hard lens. This procedure is obviously expensive and the final product does not overcome other of the known problems encountered in the extended wear of a contact lens.

Another approach to the problem has been the use of permeable lenses fabricated from silicone resins and copolymers of silicone resins with methyl methacrylate. This approach has not met with success insofar as extended wear is concerned because of the weight of the lens and the damage resulting to the bulbar conjunctivia as a consequence of the weight as described above.

Additional research has been performed both on lens materials and lens design in an effort to achieve a lens suitable for continuous wear. However, it is believed that no lens now available avoids the disadvantages inherent in continuous wear as described above.

DEFINITION OF TERMS

For purposes of definition herein, the term "daily wear lens" and like terms are intended to mean a lens normally worn during open-eye periods but not during closed-eye periods (i.e., during periods of sleep). The term "continuous wear lens" and like terms are intended to mean a lens that may be worn as a daily wear lens if desired but which can also be worn for extended periods of time (i.e., both during open-eye and closed-eye periods), if desired.

STATEMENT OF THE INVENTION

It is accordingly an object of this invention to provide a hydrogel contact lens of novel design.

Another object of the invention is to provide a minus prescription hydrogel contact lens that can be worn on a continuous basis, if desired, without removal from the eye, both during opened-eye and closed-eye periods without damage to the cornea.

Another object of this invention is to provide a hydrogel minus prescription contact lens which can be removed from the eye by the patient, handled and reinserted in the eye without damage to the lens.

A further object of this invention is to provide a hydrogel minus prescription contact lens capable of continuous wear which lens permits oxygen diffusion to the cornea in sufficient quantity to avoid the adverse effects of oxygen deprivation; avoids the physiological complications arising from damage to the bulbar conjunctivia due to compression of the limbal capillaries; and avoids corneal-scleral wetting deficiencies.

An additional object of this invention is to provide a minus prescription hydrogel contact lens intended for daily wear.

A still further object of this invention is to provide a hydrogel minus prescription contact lens capable of continuous wear without discomfort and in many cases, without the patient's being aware of the presence of the lens in the eye.

An additional object of the invention is to provide a hydrogel minus prescription contact lens which conforms to the shape of the eye.

The objects of the invention are accomplished with a combination of design features and hydrogel properties that enable fabrication of the lens in substantially reduced cross-sectional thickness and mass (weight). In this respect, the maximum cross-sectional thickness of the lens does not exceed 0.15 mm for a daily wear lens and 0.10 mm for a continuous wear lens. Other design features of the lens include a minimum diameter of at least 12 mm and preferably, ranging between 13 and 17 mm; a reduced posterior peripheral curve width not to exceed 1.5 mm and preferably, total elimination of all posterior peripheral curves so that the base curve is a monocurve that is smooth, uninterrupted and preferably spherical; an anterior lenticular curve preferably extending from the edge of the optical zone to the periphery of the lens and having a radius such that the edge thickness of the lens does not exceed 0.08 mm and preferably, does not exceed 0.06 mm; and physical properties such that the lens is capable of handling and conforming to the curvature of the eye, at least in the periphery of the lens.

The hydrogel used for lens construction is one capable of containing at least 35% water of hydration and must be sufficiently rigid so as to maintain its shape in the required thin cross section while conforming to the eye. A preferred class of suitable materials is disclosed in United States Patent Application Ser. No. 685,996, supra.

DESCRIPTION OF THE DRAWING

With reference to the drawing, there is shown a cross section of a hydrated minus soft lens fabricated in accordance with the most preferred embodiment of the invention.

DESCRIPTION OF THE PREFERRED EMBODIMENT

The inner surface of the lens, frequently referred to as posterior surface, comprises base curve 1 having radius 2. In accordance with this invention, the base curve is preferably a monocurve—i.e., the posterior surface of the lens is smooth and of a single radius. However, as is known in the art, the base curve may be provided with one or more peripheral curves (not shown in the drawing), if desired, though this is a lesser preferred embodiment in accordance with this invention. However, if present, the peripheral curve has a maximum band width of 1.5 mm and more preferably, a maximum of 1.0 mm.

The front surface of the lens, frequently referred to as the anterior surface, comprises power or prescription curve 3 having radius 4. The width of power curve 3 is known as the optical zone of the lens (defined between points 5 and 6 of the drawing). This width is generally sufficient to cover most, preferably all, of the cornea and hence, usually varies between about 8 and 10 mm and more typically between 8½ and 9½ mm.

The anterior surface of the lens also is provided with lenticular curve 7 having radius 8. The lenticular curve extends from its junction with the optical curve to the outer periphery or edge of the lens.

The overall diameter or chord of the lens is defined as the distance between points 9 and 10. This diameter is at least 12 mm, preferably varies between 13 and 17 mm and most preferably is about 13.5 mm.

For daily wear, the lens has a maximum cross-sectional thickness at any point on its circumference not exceeding 0.15 mm, preferably not exceeding 0.10 mm and most preferably varying between about 0.05 and 0.10 mm. For continuous wear, the maximum cross-sectional thickness of the lens at any point on its circumference does not exceed 0.10 mm, preferably does not exceed 0.08 mm and most preferably varies between about 0.03 and 0.08 mm. The lenses of the subject invention are thinner than those of the prior art, and the reduced thickness represents departure from the prior art. The reduced cross-section permits increased oxygen diffusion through the lens thus avoiding corneal swelling that would otherwise result as a consequence of oxygen deprivation on the corneal surface for an extended period of time. In this respect, it should be noted that oxygen deprivation at the corneal surface is a serious problem while depriving the conjunctivia of oxygen is not a problem since it receives oxygen from the vascular system. Hence, though a lesser preferred embodiment of the invention, the cross-sectional thickness of the peripheral portion of the lens, beyond the optical zone of the lens, can be thicker than the remainder of the lens without seriously compromising corneal metabolism though it is preferred to maintain the overall cross-sectional thickness of the lens as small as possible as this reduces the mass of the lens that rests on the surface of the eye.

The edge of the lens is also of reduced cross-section and preferably edge thickness as defined between points 11 and 12 of the drawing varies between about 0.03 and 0.08 mm and more preferably, is about 0.06 mm. A reduced edge thickness within the limits set forth is desirable as the edge will not interfere with the eyelid with normal blinking and hence drying of the scleral tissue is minimized.

The radius 2 of base curve 3 is within prior art limits and is to some extent dependent upon the shape of the eye to which the lens is fitted. The radius 4 of the power curve 3 is also within the prior art and is dependent upon the correction provided by the lens. Finally, the radius 8 of the lenticular curve 7 is that necessary to provide the desired edge thickness of the lens. The lenticular curve extends from its junction with the power curve to the outermost edge of the lens and to reduce edge thickness, the curve must be steeper than the power curve. Hence, the radius 8 of the lenticular curve 7 is shorter than radius 4 of power curve 3. Preferably, radius 8 is at least 0.2 mm shorter than radius 4 and more preferably, at least 0.5 mm. It should be noted that where the lenticular curve is steeper than the power curve and particularly, in the absence of posterior peripheral curvatures, the mass of the lens is substantially reduced.

The hydrogel used to fabricate the lens is one capable of retaining its structural integrity in the thin cross-sections required for the lens, is sufficiently rigid to retain a substantially constant optical surface and is sufficiently flexible to permit the lens to conform to the surface contour of the eye. The ability to conform to the surface contour of the eye is most important as it is responsible for the lens remaining firmly affixed to the eye without substantial movement and change in optical surface as is frequently encountered with blinking. Preferably, the hydrogel has a water of hydration of at least 35% and preferably a water of hydration varying between 35 and 50% and more preferably between 40 and 46%.

Preferred hydrogels are disclosed in U.S. Patent Application Ser. No. 685,996, supra. These hydrogels are preferably a terpolymer of a hydrophilic dihydroxy acrylate, a water-insoluble acrylate and an epoxidized acrylate.

The hydrophilic dihydroxyalkyl acrylate comonomer conforms to the general formula:

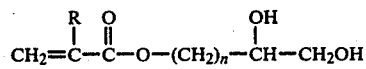

where R is hydrogen or methyl and n is a whole integer having a value of from 0 to 4, preferably from 1 to 4. A preferred dihydroxyacrylate is 2,3-dihydroxypropyl methacrylate.

The second comonomer is a substantially water insoluble alkyl acrylate or methacrylate corresponding to the general formula:

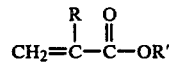

where R is hydrogen or methyl and R' is alkyl having from 1 to 6 carbon atoms. Alkyl acrylates conforming to this formula are readily available. Examples of suitable acrylates include methyl acrylate, methyl methacrylate, ethyl acrylate, ethyl methacrylate, propyl methacrylate, butyl acrylate and butyl methacrylate. Methyl methacrylate is most preferred.

The third comonomer is the epoxidized alkyl acrylate conforming to the formula:

$$CH_2=\underset{\underset{R}{|}}{C}-\underset{\underset{O}{\|}}{C}-O-(CH_2)_n-\overset{\overset{O}{\diagup \diagdown}}{CH\text{———}CH_2}$$

where R and n are as above defined. A preferred epoxidized acrylate is 2,3-epoxypropyl methacrylate.

The molar ratio of dihydroxyalkyl acrylate to alkyl acrylate varies within broad limits. Preferably, the dihydroxyalkyl acrylate at least equals or exceeds the alkyl acrylate and a preferred ratio varies between about 1:1 and 10:1, more preferably between 1.2:1.0 and 2:1. The most preferred molar ratio is about 1.5:1.0.

The amount of epoxidized acrylate used may vary within broad parameters, generally from 0 to 30% by weight of the dihydroxy acrylate, more preferably, from 0.1 to 15% by weight and most preferably, from 1.0 to 7.5% dependent upon the monomers used, their ratio and the like. A more definite amount is the amount sufficient to provide a polymer capable of adsorbing water of hydration in an amount of from 35 to 50%, and more preferably, from 40 to 46%.

It is believed that the epoxidized acrylate acts as a cross-linking agent for the polymer. In this respect, other cross-linking agents may be included in the formulation both with and without the epoxidized acrylate, such cross-linking agents including diesters of acrylic and methacrylic acid, especially glycol diesters such as ethylene glycol dimethacrylate, propylene glycol dimethacrylate, ethylene glycol acrylate and the like, as well as derivatives thereof such as triethanolamine dimethacrylate, triethanolamine trimethacrylate, tartaric acid dimethacrylate, triethylene glycol dimethacrylate, the dimethacrylate of bishydroxyethylacetamide, and the like. The amount of cross-linking agent is dependent upon obtaining the desired rigidity as described above. In general, the concentration does not exceed 5% of the total monomer constituents, preferably ranges between about 0.1 to 4% and should be in an amount sufficient to yield a hydrogel from the polymer having the above hydration properties.

The polymers are formed by bulk polymerization using suitable catalysts. The monomers are mixed in the absence of solvent and maintained under reduced pressure at an elevated temperature for a period of time sufficient to solidify the reaction mixture. Typically, the temperature of reaction varies between 20° and 60° C. The catalyst concentration may vary within broad limits dependent upon the particular catalyst used, but generally varies between about 0.001 and 0.2 weight percent of the hydroxyalkylacrylate, and preferably between 0.01 and 0.04 weight percent. A preferred catalyst is isopropyl percarbonate in an amount of about 0.02 weight percent.

Other suitable lens materials would be obvious to those skilled in the art given the property requirements set forth herein. Thus, for example, the polymers formed by the polymerization of 2-hydroxyethyl methacrylate is described in U.S. Pat. No. 3,220,960, supra, could be made suitable by an increase in the concentration of cross-linking agent so that a more highly cross-linked structure and hence, a more rigid hydrogel, would be obtained.

We claim:

1. A soft minus prescription hydrogel contact lens, said lens having a maximum cross-sectional thickness at any point not exceeding 0.15 mm and being of a hydrogel sufficiently rigid so as not to irreversibly deform during blinking and sufficiently flexible so as to conform to the curvature of the eye.

2. The lens of claim 1 where the maximum cross-sectional thickness does not exceed 0.10 mm at any point.

3. The lens of claim 1 capable of continuous wear and having a maximum cross-sectional thickness that varies between about 0.03 and 0.08 mm.

4. The lens of claim 1 capable of daily wear and having a maximum cross-sectional thickness that varies between about 0.05 and 0.10 mm.

5. The lens of claim 3 where the diameter varies between 13 and 17 mm.

6. The lens of claim 5 where the diameter is about 13.5 mm.

7. The lens of claim 3 where the posterior curve is a monocurve.

8. The lens of claim 3 where the edge thickness of the lens varies between about 0.03 and 0.08 mm.

9. The lens of claim 8 where edge thickness is about 0.06 mm.

10. The lens of claim 1 having a lenticular curve extending from its junction with the power curve to the edge of the lens, the radius of said lenticular curve being at least 0.2 mm shorter than the radius of the power curve.

11. A soft minus prescription hydrogel contact lens, said lens having a maximum cross-sectional thickness at any point not exceeding 0.15 mm, a minimum diameter of 12 mm, an edge thickness ranging between 0.03 and 0.08 mm and a lenticulated curve extending from its junction with the power curve to the edge of the lens, said lenticular curve having a radius of at least 0.02 mm shorter than the radius of the power curve, said lens being of a hydrogel containing water of hydration in an amount of at least 35% by weight of the total weight of the hydrated lens and being sufficiently rigid so as not to irreversibly deform during blinking and sufficiently flexible to conform to the contour of the eye.

12. The lens of the claim 11 where the posterior curve of the lens is a monocurve.

13. The lens of claim 12 where the maximum cross-sectional thickness of the lens does not exceed 0.10 mm at any point on its circumference.

14. The lens of claim 12 capable of continuous wear and having a maximum cross-sectional thickness that varies between 0.03 and 0.08 mm.

15. The lens of claim 12 capable of daily wear and having a maximum cross-sectional thickness that varies between 0.05 and 0.10 mm.

16. The lens of claim 12 where the diameter varies between 13 and 17 mm.

17. The lens of claim 16 where the diameter is about 13.5 mm.

18. The lens of claim 12 where the edge thickness of the lens varies between about 0.03 and 0.08 mm.

19. The lens of claim 12 where the hydrogel is a hydrated terpolymer of a dihydroxyalkyl acrylate or methacrylate in major amount, an alkyl acrylate or methacrylate in minor amount and an epoxidized alkyl acrylate or methacrylate in an amount to impart the sufficient rigidity to the hydrogel.

20. The lens of claim 19 where the dihydroxyalkyl acrylate or methacrylate is glyceryl methacrylate, the alkyl acrylate or methacrylate is methyl methacrylate and the epoxidized alkyl acrylate or methacrylate is glycidyl methacrylate.

21. The lens of claim 19 where the hydrogel also includes a diester of an acrylic or methacrylic acid as a cross-linking agent.

22. The lens of claim 21 where the diester is a diester of glycol and methacrylic acid.

23. The lens of claim 21 where the diester is ethylene glycol dimethacrylate.

24. The lens of claim 21 where the diester is present in an amount of up to 5% weight of all monomers.

25. The lens of claim 24 where the diester is present in an amount of from 0.1 to 4%.